US008777889B2

(12) United States Patent
Joshi et al.

(10) Patent No.: US 8,777,889 B2
(45) Date of Patent: *Jul. 15, 2014

(54) APPARATUS AND METHOD FOR ADMINISTERING A THERAPEUTIC AGENT INTO TISSUE

(75) Inventors: Ashok V Joshi, Salt Lake City, UT (US); James Steppan, Park City, UT (US); Jesse A Nachlas, Salt Lake City, UT (US); Kieran P Murphy, Baltimore, MD (US)

(73) Assignee: Ceramatec, Inc., Salt Lake City, UT (US)

( * ) Notice: Subject to any disclaimer, the term of this patent is extended or adjusted under 35 U.S.C. 154(b) by 1284 days.

This patent is subject to a terminal disclaimer.

(21) Appl. No.: 11/193,339

(22) Filed: Aug. 1, 2005

(65) Prior Publication Data

US 2007/0025890 A1 Feb. 1, 2007

Related U.S. Application Data

(63) Continuation-in-part of application No. 10/867,215, filed on Jun. 15, 2004, now Pat. No. 7,615,030.

(51) Int. Cl.
*A61M 37/00* (2006.01)
(52) U.S. Cl.
USPC ............... 604/25; 604/23; 604/181; 604/187
(58) Field of Classification Search
USPC .................. 604/181, 184, 187, 23–26, 890.1, 604/891.1, 143–147; 128/202.25; 422/186.07, 186.12

See application file for complete search history.

(56) References Cited

U.S. PATENT DOCUMENTS

| | | |
|---|---|---|
| 2,032,723 A | 3/1936 | Schweser |
| 3,682,162 A | 8/1972 | Colyer |
| 4,128,173 A | 12/1978 | Lazarus et al. |
| 4,193,397 A | 3/1980 | Tucker et al. |
| 4,485,815 A | 12/1984 | Amplatz et al. |
| 4,632,980 A | 12/1986 | Zee et al. |
| 4,644,960 A | 2/1987 | Johans |
| 4,743,199 A | 5/1988 | Weber et al. |
| 4,938,233 A | 7/1990 | Orrison |
| 5,052,382 A | 10/1991 | Wainwright |

(Continued)

FOREIGN PATENT DOCUMENTS

| | | | |
|---|---|---|---|
| DE | 447936 | * | 7/1927 |
| DE | 2543284 | | 3/1977 |

(Continued)

OTHER PUBLICATIONS

"Medizone Patents and Trademarks", Sep. 13, 2002: 1 of 2. http://www.medizoneint.com/patents.html.

(Continued)

*Primary Examiner* — Aarti B Berdichevsky
*Assistant Examiner* — Laura Schell
(74) *Attorney, Agent, or Firm* — David Fonda

(57) ABSTRACT

An apparatus for administering a therapeutic is provided. In various embodiments, the apparatus includes a syringe having a barrel and a plunger and having an ozone generator associated therewith. The generator is initiated and a therapeutic gas is accumulated within the barrel, at which point it can be delivered from the barrel into a target site via a needle, thereby delivering therapeutic effects to that target site.

6 Claims, 13 Drawing Sheets

(56) References Cited

U.S. PATENT DOCUMENTS

| | | |
|---|---|---|
| 5,078,714 A | 1/1992 | Katims |
| 5,106,589 A | 4/1992 | Conrad |
| 5,163,904 A | 11/1992 | Lampropoulos et al. |
| 5,439,452 A | 8/1995 | McCarty |
| 5,536,241 A | 7/1996 | Zapol |
| 5,540,898 A | 7/1996 | Davidson |
| 5,674,195 A | 10/1997 | Truthan |
| 5,797,872 A | 8/1998 | Ogata et al. |
| 5,868,999 A | 2/1999 | Karlson |
| 5,900,127 A | 5/1999 | Iida et al. |
| 5,971,722 A | 10/1999 | Maget et al. |
| 6,071,280 A | 6/2000 | Edwards et al. |
| 6,073,627 A | 6/2000 | Sunnen |
| 6,086,552 A | 7/2000 | Bolton |
| 6,103,190 A | 8/2000 | Tanimura et al. |
| 6,110,431 A * | 8/2000 | Dunder .................... 422/186.12 |
| 6,134,806 A | 10/2000 | Dhaemers |
| 6,136,308 A | 10/2000 | Tremblay et al. |
| 6,204,058 B1 | 3/2001 | Bolton |
| 6,251,090 B1 | 6/2001 | Avery et al. |
| 6,391,183 B1 | 5/2002 | Tanioka et al. |
| 6,398,928 B1 | 6/2002 | Koganezawa et al. |
| 6,399,664 B2 | 6/2002 | Smith |
| 6,413,228 B1 | 7/2002 | Hung et al. |
| 6,620,379 B1 | 9/2003 | Piuk et al. |
| 6,632,222 B1 | 10/2003 | Edwards et al. |
| 6,800,064 B2 | 10/2004 | Liang |
| 6,810,288 B2 | 10/2004 | Joshi |
| 6,875,018 B2 | 4/2005 | Lynch et al. |
| 6,912,417 B1 | 6/2005 | Bernard et al. |
| 7,244,354 B2 | 7/2007 | Burris et al. |
| 7,615,030 B2 * | 11/2009 | Murphy et al. ................. 604/25 |
| 8,066,659 B2 | 11/2011 | Joshi et al. |
| 8,066,695 B2 | 11/2011 | Muto et al. |
| 8,162,873 B2 | 4/2012 | Muto et al. |
| 2002/0037235 A1 | 3/2002 | Khatchatrian et al. |
| 2002/0133148 A1 | 9/2002 | Daniel et al. |
| 2002/0188323 A1 | 12/2002 | Penner et al. |
| 2003/0050674 A1 * | 3/2003 | Joshi .............................. 607/50 |
| 2003/0084907 A1 | 5/2003 | Pacek et al. |
| 2003/0176834 A1 | 9/2003 | Horth et al. |
| 2004/0071615 A1 | 4/2004 | Khatchatrian et al. |
| 2004/0092905 A1 | 5/2004 | Azzolini |
| 2004/0133188 A1 | 7/2004 | Vardi et al. |
| 2004/0245087 A1 | 12/2004 | Lee |
| 2004/0254525 A1 | 12/2004 | Uber et al. |
| 2005/0010069 A1 | 1/2005 | Fitchett et al. |
| 2005/0023371 A1 | 2/2005 | Joshi et al. |
| 2005/0074501 A1 * | 4/2005 | Murphy et al. ................ 424/600 |
| 2005/0203503 A1 | 9/2005 | Edwards et al. |
| 2005/0277912 A1 | 12/2005 | John |
| 2006/0095026 A1 | 5/2006 | Ricart et al. |
| 2006/0166088 A1 | 7/2006 | Hokanson et al. |
| 2006/0251551 A1 | 11/2006 | Johnson |
| 2007/0025890 A1 | 2/2007 | Joshi et al. |
| 2007/0154363 A1 | 7/2007 | Joshi et al. |
| 2008/0004615 A1 | 1/2008 | Woloszko et al. |
| 2008/0009847 A1 | 1/2008 | Ricart et al. |
| 2008/0167650 A1 | 7/2008 | Joshi et al. |
| 2009/0204062 A1 | 8/2009 | Muto et al. |
| 2009/0209902 A1 | 8/2009 | Muto et al. |
| 2010/0307928 A1 | 12/2010 | Joshi et al. |
| 2010/0312171 A1 | 12/2010 | Joshi et al. |
| 2012/0022437 A1 | 1/2012 | Joshi et al. |
| 2012/0022438 A1 | 1/2012 | Joshi et al. |
| 2012/0150173 A1 | 6/2012 | Joshi et al. |

FOREIGN PATENT DOCUMENTS

| | | |
|---|---|---|
| JP | 08-150213 | 6/1996 |
| JP | 11-292512 | 10/1999 |
| JP | 2001506172 | 5/2001 |
| JP | 2005307232 | 11/2005 |
| WO | 96/08280 | 3/1996 |
| WO | WO-98/10774 | 3/1998 |
| WO | WO 01/50983 | 7/2001 |
| WO | WO 02/076533 | 10/2002 |
| WO | WO-2004103452 | 12/2004 |
| WO | WO-2005032387 | 4/2005 |

OTHER PUBLICATIONS

Andreula, Cosma, et al. "Interventional Spinal Procedures", *European Journal of Radiology 50* (2004):112-119.

Andreula, Cosma F., et al. "Minimally Invasive Oxygen-Ozone Therapy for Lumbar Disk Herniation." *American Journal of Neuroradiology 24* (2003): 996-1000.

Bocci, V. "Biological and Clinical Effects of Ozone. Has Ozone Therapy a Future in Medicine?" *British Journal of Biomedical Science 56* (1999): 270-279.

Bocci, Velio. *Oxygen-Ozone Therapy: A Critical Evaluation*. The Netherlands: Kluwer Academic Publishers, 2002. 43-46.

Bocci, V., et al. "Ozone in Medicine." *Ozone Science & Engineering 23* (2001): 207-217.

Bocci, Velio. *Ozone: A New Medical Drug*. The Netherlands: Springer, 2005. 9-11.

Sunnen, Gerard, "Ozone in Medicine Bibliography." Sep. 1999: 1,3,5,7 of 8. http://www.medizoneint.com/biblio.html.

McCabe, Ed "Scientific and Medical References Proving Ozone's Validity as a Medical Treatment", http://www.ozonetherapy.co.uk/articles/ed__mccabe__ozone__history__and__references.htm, 1994, Retrieved Oct. 7, 2004, (1994).

Morello, Gaetano "Ozone Therapy: New Breakthrough for Back Treatment", http://allergytalk.com/6/ca__3.htm, Retrieved Oct. 8, 2007., 1.

Muto, Mario et al., "Percutaneous Treatment of Herniated Lumbar Disc By Intradiscal Oxygen-Ozone Injection", *Interventional Neuroradiology 4*:279-286, 1998, 279-286.

Schultz, O. Abstract and International Search Report for WO2005032387, (Mar. 2, 2005), 1-6.

European Patent Office Automated Translation of DE2543284, (Oct. 5, 2007), 1-4.

Williams, Catherine S. Office Action for U.S. Appl. No. 10/867,215 sent Jul. 18, 2007, 1-8.

Williams, Catherine S. Office Action for U.S. Appl. No. 10/867,215 sent Aug. 17, 2007, 1-2.

Schultz, O. PCT International Search Report for PCT/IB2004/003706, (Jun. 3, 2005), 1-6.

Schultz, O. PCT Written Opinion of the International Searching Authority for PCT/IB2004/003706, (Jun. 3, 2005), 1-10.

Young, Lee W., PCT International Search Report for PCT/US06/28425, (Jul. 31, 2007), 1-2.

Young, Lee W., PCT Written Opinion of the International Searching Authority for PCT/US06/28525, (Jul. 31, 2007), 1-4.

Young, International Search Report for PCT/US07/25989 sent Mar. 27, 2008, 1-2.

Young, Written Opinion for PCT/US07/25989 sent Mar. 27, 2008, 1-6.

Stigell, Office Action for U.S. Appl. No. 10/867,215 sent Apr. 1, 2008, 1-8.

Stigell, Office Action for U.S. Appl. No. 10/867,215 sent Oct. 16, 2008, 1-6.

Stigell, Theodore J., "Notice of Allowability for U.S. Appl. No. 10/867,215 Mailed Apr. 7, 2009", 1-4.

Stigell, Theodore J., "Notice of Allowability for U.S. Appl. No. 10/867,215 Mailed on Aug. 6, 2009", 1-4.

Schultz, Ottmar "European Office Action for App. No. EP08/004367 Completed May 7, 2008", 1-6.

Schultz, Ottmar "European Office Action for App. No. EP 08/004372 Completed May 8, 2008", 1-8.

Bumgarner, Melba "Office Action for U.S. Appl. No. 11/616,041 Mailed on Sep. 17, 2009", 1-7.

Smith, Kaitlyn E., "Non-final Office Action", Non-final office action for U.S. Appl. No. 12/052,617, (Apr. 11, 2012), 1-8.

Stigell, Theodore J., "Non-Final Office Action", Non-Final Office Action of U.S. Appl. No. 12/429,736, (Nov. 4, 2011), 1-7.

(56) References Cited

OTHER PUBLICATIONS

Stigell, Theodore J., "Final Office Action", Final Office Action for U.S. Appl. No. 12/429,736, (Feb. 21, 2012), 1-8.
Stigell, Theodore J., "Non-Final Office Action", Non-Final Office Action for U.S. Appl. No. 12/431,062, (Jan. 18, 2012), 1-10.
Umehara, Makiko "Examiner's First Report (AU)", Examiner's First Report for AU application No. 2010206008 (corresponding to U.S. Appl. No. 12/429,736), (Feb. 24, 2011), 1-2.
Umehara, Makiko "Examiners Report No. 2 (AU)", Examiners Report No. 2 (AU) for app. No. 2010204467 (corresponding to U.S. Appl. No. 12/430,740), (Mar. 29, 2012), 1-2.
McTavish, Megan "Office Action (CA)", Office Action/Notification of Requisition (CA) for app. No. 2612541 (corresponding to U.S. Appl. No. 11/193,339), (Aug. 25, 2011), 1-3.
Tanaka, Reiko "Notice of Reasons for Rejection", Notice of Reasons for Rejection (JP) and Translation for app No. 2000-544036 (corresponding to U.S. Appl. No. 11/616,041), (Jan. 24, 2012), 1-8.
"Translation of Japanese Office Action", JP App. No. 2008-525006, (Jun. 21, 2011),1-11.
Osinski, Bradley J., "Notice of Allowance", U.S. Appl. No. 11/616,041, (Aug. 12, 2011),1-5.
Pfeiffer, Uwe "EP Search Report", App. No. 09722670, (Jun. 17, 2011), 1-6.
Stigell, Theodore "USPTO Office Action", U.S. Appl. No. 12/430,740, (Aug. 12, 2011),1-9.
Osinski, Bradley "Office Action for U.S. Appl. No. 11/616,041", (May 25, 2011),1-9.
Osinski, Bradley J., "Office Action for U.S. Appl. No. 11/616,041", (Nov. 5, 2010),1-11.
Schell, "Office Action for U.S. Appl. No. 11/193,339 sent Dec. 3, 2008", (Dec. 3, 2008),1-10.
Stigell, Theodore J., "Office Action for U.S. Appl. No. 12/430,740", (Oct. 14, 2010),1-11.
Stigell, Theodore J., "Office Action for U.S. Appl. No. 12/430,740", Feb. 22, 2011),1-6.
Stigell, Theodore J., "Office Action for U.S. Appl. No. 12/431,089", (Feb. 18, 2011),1 -7.
Jeon, Chang "International Search Report", PCT Application No. 2009/037413, (Nov. 3, 2009), 1-4.
Jeon, Chang "Written Opinion of the International Searching Authority", PCT Application No. 2009/037413, (Nov. 3, 2009),1-5.
Schell, Laura "Non-Final Office Action", U.S. Appl. No. 11/193,339, (Jan. 19, 2010),1-9.
Bumgarner, Melba "Non-Final Office Action", U.S. Appl. No. 11/616,041, (Mar. 10, 2010),1-12.
Stigell, Theodore "Non-Final Office Action", U.S. Appl. No. 12/430,740, (May 26, 2010),1-8.
Schell, Laura "Final Office Action", U.S. Appl. No. 11/193,339, (Jul. 14, 2010),1-12.
Mayekar, Kishor "Non-Final Office Action", U.S. Appl. No. 12/816,787, (Sep. 25, 2012),1-6.
Stigell, Theodore J., "Non-Final Office Action", U.S. Appl. No. 12/431,062, (Jul. 11, 2012),1-8.
Singh, Vijay "Examiner's First Report on Patent Application 2007342491", Australian Patent Application 2007342491, (May 15, 2012),1-3.
McTavish, Megan "Notice of Requisition", CA App. No. 2,612,541 (Corresponding to U.S. Appl. No. 11/193,339), (Jul. 9, 2012),1-2.
Unknown Japanese Examiner, "Notice of Reasons for Rejection", JP App. No. 2011-278004, (Feb. 12, 2013),1-2.
Okada and Associates, "Translation of Notice of Reasons for Rejection", JP App. No. 2011-278004, (Feb. 14, 2013),1-2.
Unknown, "Machine Translation of JP 08-150213", JP Patent publication 08-150213, (Jun. 11, 1996),1-6.
Izumi, et al., "English Abstract for JP 11-292512", Japanese Patent publication JP 11-292512, (Oct. 26, 1999),1-2.
Unknown Japanese Examiner, "Notice of Reasons for Rejection", JP App. No. 2011-500900 (Corresponding to U.S. Appl. No. 12/052,617), (Feb. 5, 2013),1-3.
Okada and Associates, "Translation of Notice of Reasons for Rejection", JP App. No. 2011-500900 (Corresponding to U.S. Appl. No. 12/052,617), (Feb. 13, 2013),1-2.
Walsh, et al., "English Abstract for JP2001506172", Espacenet English Abstract for WO9904850, Corresponding to JP Patent Publication JP 2001506172, (May 15, 2001),1.
Maeda, et al., "English Abstract for JP2005307232", Espacenet English Abstract for JP2005307232, (Nov. 4, 2005),1-2.
Osinski, Bradley J., "Non-Final Office Action", U.S. Appl. No. 13/189,290, (Dec. 5, 2012),1-9.
Osinski, Bradley J., "Non-Final Office Action", U.S. Appl. No. 13/188,999, (Dec. 14, 2012),1-7.
Viidebaum, Mikk "Extended European Search Report", EP App. No. 087863148.8 (corresponding to U.S. Appl. No. 11/616,041), (Nov. 28, 2012),1-8.
Osinkski, Bradley J., "Notice of Allowance", U.S. Appl. No. 13/189,290, (Aug. 8, 2013),1-13.
Mayekar, Kishor "Non-Final Office Action", U.S. Appl. No. 13/793,889, (Aug. 20, 2013),1-20.

* cited by examiner

APPARATUS AND METHOD FOR ADMINISTERING A THERAPEUTIC AGENT INTO TISSUE

This application is a continuation-in-part of prior application Ser. No. 10/867,215, filed Jun. 15, 2004, and entitled "Apparatus and method for administering a therapeutic agent into tissue," now issued as U.S. Pat. No. 7,615,030 which application is hereby incorporated by reference.

FIELD OF THE INVENTION

The present invention relates generally to an apparatus for administering a therapeutic agent into tissue and in particular, for the administration of a gaseous therapeutic agent such as an oxidizing gas or an inert gas.

BACKGROUND OF THE INVENTION

Back joint disc or tendon pain is a common and potentially debilitating ailment that affects an estimated 80% of the worldwide population at least once in a lifetime. In many instances, the cause of the pain can be attributed to a degenerated intervertebral disc that has further deteriorated into a condition known as disc herniation. This occurs when the disc nucleus pulposus extrudes through a tear or fissure in the outer lining of the disk, thereby exerting pressure on spinal nerves. The compression caused by the herniated nucleus leads to inflammation and is directly responsible for the pain felt down the leg (also referred to as sciatica). Available treatments for this type of back pain vary according to the severity of the hernia. If mild, the patient's condition can be appeased with rest and inactivity for an extended period of time. However, for patients suffering from a severe herniation or who do not respond to non-invasive treatment (pharmacological and/or physical therapy), surgical intervention is often recommended. With this invasive treatment come several disadvantages such as:
  i) irreversibility of the procedure
  ii) formation of scar tissue
  iii) slower recovery time
  iv) longer hospital stays Since the late 1950s, many attempts have been made to treat sciatica and lower back pain with percutaneous procedures to avoid surgery. Well known treatments for example are percutaneous discetomy and chemonucleolysis but the cost of these procedures has kept researchers looking for another alternative. It was in 1984 that an Italian orthopedic surgeon by the name of Dr. Cesare Verga first proposed the use of ozone/oxygen mixtures to treat the pathology of a herniated disk. (See for example, http://www.cleanairassociationlcom/6/ca_3.htm, Ozone Therapy: New breakthrough for Back Treatment, by Gaetano Morello, M.D., the contents of which are incorporated herein by reference.)

Other prior art references include: Percutaneous Treatment of Herniated Lumbar Disc by Intradiscal Oxygen-Ozone Injection, M. Muto and F. Avella, Interventional Neuroradiology 4:279-286, 1998.

In other situations such as rheumatoid arthritis, osteoarthritis or a repetitive injury through sports or occupation, such as tennis elbow, frozen shoulder, or house maids knee, inflammation can develop between the two surfaces that are involved in allowing joint function, such as a tendon and the sheath or lubricated tube in which that tendon moves. Inflammation such as bursitis in the knee shoulder hip, or other anatomic bursa may benefit from the administration of a therapeutic agent such as oxygen-ozone mixtures or excited, energetic, pure oxygen, this includes epicondylitis, and other tendonitis and bursitis, including the wrist, hand and the tendon sheaths of the hand and wrist. Inflammation can occur at a site where a tendon or a ligament insert to bone or pass through a sheath from trauma, tension, over use or disease.

Inflammation can develop through pathologies of any joint, and these may again include the inflammatory arthropatic conditions of rheumatoid arthritis, psoriatic arthritis and the like, or osteoarthritis. Joints that may be involved in these processes that are amenable to the administration of a therapeutic agent such as oxygen-ozone mixtures or excited, energetic, pure oxygen include the synovial joints such as the, temperomandibular joint, the hip joint, knee joint, ankle joint, elbow joint or sacro-iliac joint. Vertebral facet and sacro-iliac joints may also benefit, inflammatory involvement of joints in the hand, wrist and feet with rheumatoid arthritis, osteoarthritis or a repetitive injury through sports or occupational such as carpal tunnel syndrome.

The inflammatory and arthritic or degenerative discussions described above are usually treated with a combination of anti-inflammatory agents such as ibuprofen, or more powerful drugs such as steroids or chemotherapy such as methotrexate. It is a common medical practice to inject steroid medications or lidocaine directly into the inflamed tissue or joint. This is often done repeatedly. These drugs can be associated with side effects of infection and even death from gastric ulcer bleeding or immunosurpression and infection. We believe that ozone therapy whether with oxygen-ozone mixtures or excited, energetic, pure oxygen as a gas or dissolved in a liquid has advantages over the current practice.

Lavage of a surgical space prior to placement of a permanent surgical implant such as a hip or knee prosthesis, or pacemaker or treatment of an infected joint can be facilitated by the use of oxygen-ozone mixtures or excited, energetic, pure oxygen as a sterilizing substance. Similarly a colostomy stoma can be created such that the adhesive disk is infused with oxygen-ozone mixtures or excited, energetic, pure oxygen as a gas or dissolved in a liquid to aid in healing and inhibit infection. The post surgical recovery from sternotomy after cardiac surgery is often complicated by wound infection. Placement of a resorbable catheter in the wound that could be irrigated with oxygen-ozone mixtures or excited, energetic, pure oxygen as a gas or dissolved in a liquid would aid healing. Indeed any wound could have a resorbable multisided hole catheter placed in it to allow oxygen-ozone mixtures or excited, energetic, pure oxygen to be injected through it. This would have anti-infective, analgesic, and wound-healing properties thereby shortening recovery time and decreasing complication rates after surgery.

Oxygen-ozone mixtures or excited, energetic, pure oxygen as a gas or dissolved in a liquid could be applied to the wound /surgical site healing at a site of high probability of infection such an abdominal incision/wound after appendectomy, or urgent colectomy with colostomy or after percutaneous endoscopic cholecystectomy.

Endoscopic procedural infusion of ozone and trans catheter infusion of ozone can be used to inhibit the complications endoscopic medical intervention or image guided or non-image guided catheter based intervention for example in endoscopic evaluation of the pancreatic duct.

Dental injection of oxygen-ozone mixtures or excited, energetic, pure oxygen as a gas or dissolved in a liquid may augment the preparation and repair of dental cavities, and aid in reduction of root canal inflammation or periodontal disease.

There are veterinary applications of minimally invasive administration of oxygen-ozone mixtures or excited, energetic, pure oxygen as a gas or dissolved in a liquid in animals diseased with disc and degenerative syndromes. Few other options are available in that arena. Some animals are destroyed due to debilitating pain secondary to pain from disc disease, and arthritis.

While the full therapeutic potential of oxygen-ozone mixtures or excited, energetic, pure oxygen continues to unfold with ongoing research, it is already clear that this form of therapy for the treatment of disc herniation has significant advantages over other surgical and percutaneous procedures. Some of these advantages include:

fewer clinical and neuroradiological contraindications
success rates greater than about 70% in the intervertebral disc
little or no recovery time
little or no side effects
little or no scar tissue formed
minimally invasive procedure
effective alternative treatment for which response to conservative management, such as rest and reduced daily activity, has failed to treat As the success of ozone gas therapy continues to gain recognition in the medical arena as a non-invasive alternative for the treatment of disc herniation, current methods of administering an effective dose of the ozone are solely as a gas and are far from optimum. For example, SPM Recovery Technologies Ltd. (http://www.spm.co.il); U.S. Pat. No. 6,073,627; and an article from American Health Magazine (January 1988, p. 16), all disclose equipment for treatment of wounds with ozone. However, these equipment are often bulky, cumbersome, power intensive, difficult to maintain, clean, calibrate, and very costly. These equipment also lack a sterile methodology through which the ozone can be delivered selectively to the pain-affected area, i.e. the herniated disk. The gas is unstable with a half life measured in minutes. There are no dedicated medical ozone generators that are disposable, single-use units. Thus, there is a need for equipment specifically designed for the treatment of disc herniation and other medical conditions affecting the body with oxygen-ozone mixtures or excited, energetic, pure oxygen so that it can be done in an efficient and sterile manner. There is a need to develop kits for intervention in inflammatory and degenerative disease, that are portable, disposable, or reusable, but aid in creating sterile, stable, ozone rapidly on demand.

SUMMARY OF THE INVENTION

It is therefore an object of the present invention to provide a novel apparatus and method for administering a gas into a tissue that obviates or mitigates at least one of the disadvantages of the prior art.

An aspect of the invention provides a syringe comprising a barrel and a plunger for insertion into a first end of the barrel and delivering the agent from a second end of the barrel. The syringe also comprises a generator attached to one of the plunger and the barrel, the generator for producing a therapeutic agent. The syringe also includes an accumulator within the barrel having an accumulation configuration in communication with the generator for accumulating the agent. The accumulator has a delivery configuration placing the accumulator in communication with the second end. The accumulator is automatically changeable from the accumulation configuration to the delivery configuration when a desired level of agent has been generated in the accumulator such that the agent can be delivered from the second end of the barrel.

The gaseous therapeutic agent can be an oxidizing gas or an inert gas or combinations thereof.

An oxidizing gas which can include oxygen ($O_2$); a mixture containing oxygen plus ozone ($O_3$); oxygen radicals; hydroxyl radicals; ionic oxygen; oxygen treated with energy; and/or combinations any of the foregoing.

Inert gases can include, but are not limited to, nitrogen, helium, carbon dioxide, and/or combinations thereof.

The generator can be a corona discharge device, and in which case the accumulator can be an interior space within the barrel containing oxygen. The plunger can thus include a dc power source (such as a battery) and electronics to generate and deliver the high-voltage, high-frequency ac electrical signal to the generator. A frequency of the signal can be between about one tenth of a kilohertz ("kHz") and about one thousand kHz; or between about twenty kHz and about sixty kHz. The voltage of the electrical signal can be between about one kilovolt and about twenty kilovolts; or a voltage of the electrical signal can be between about three kilovolts and about six kilovolts. The ambient temperature of the oxygen can be between about fifteen ° C. and about thirty ° C.; or the ambient temperature of the oxygen can be between about twenty ° C. and about twenty-five ° C.

The generator can be an ultraviolet ("UV") light source, and in which case the accumulator can be an interior space within the barrel containing oxygen. The plunger can thus include a dc power source (such as a battery) and electronics to generate and deliver the signal to the UV light source. The wavelength of the light source can be between about 100 nm and about 700 nm; or between about 140 nm and about 200 nm.

In other aspects, the generator can be an open vessel for storing an ozonated gel and a heating element, such that activation of the heating element elevates a temperature of the gel causing desorption of ozone-oxygen mixture from the gel. The gel can be formed by sparging ozone through olive oil and then chilling the olive oil. The olive oil is chilled to a temperature of between about minus fifteen ° C. and about ten ° C.

Another aspect of the invention provides a generator for producing therapeutic oxygen-ozone mixtures, the generator comprising an attachment point for affixing the generator to one of a plunger and a barrel. The barrel has a first end for receiving the plunger and a second end for delivering the oxygen-ozone mixture therefrom upon depression of the plunger. The generator communicates with an accumulator disposed within the barrel. In an accumulation configuration, the oxygen-ozone mixture accumulates inside the accumulator. The accumulator also has a delivery configuration placing the accumulator in communication with the second end of the barrel. The accumulator is automatically changeable from the accumulation configuration to the delivery configuration when a desired level of agent has been generated in the accumulator such that the agent can be delivered from the second end.

The generator can comprise a vessel for housing an ozonated gel and a heating element for increasing a temperature of the gel to cause desorption of an oxygen-ozone mixture therefrom.

The generator can comprise an electrical chemical cell.

The generator can comprise a corona discharge device.

The generator can comprise an ultraviolet light source.

Aspects of the invention also include methods for generating therapeutic agents using the apparatuses taught herein, and methods of administering a therapeutic agents using the apparatuses taught herein.

BRIEF DESCRIPTION OF THE DRAWINGS

The present invention will now be explained, by way of example only, with reference to certain embodiments and the attached figures in which.

DETAILED DESCRIPTION OF THE INVENTION

Figure 1:
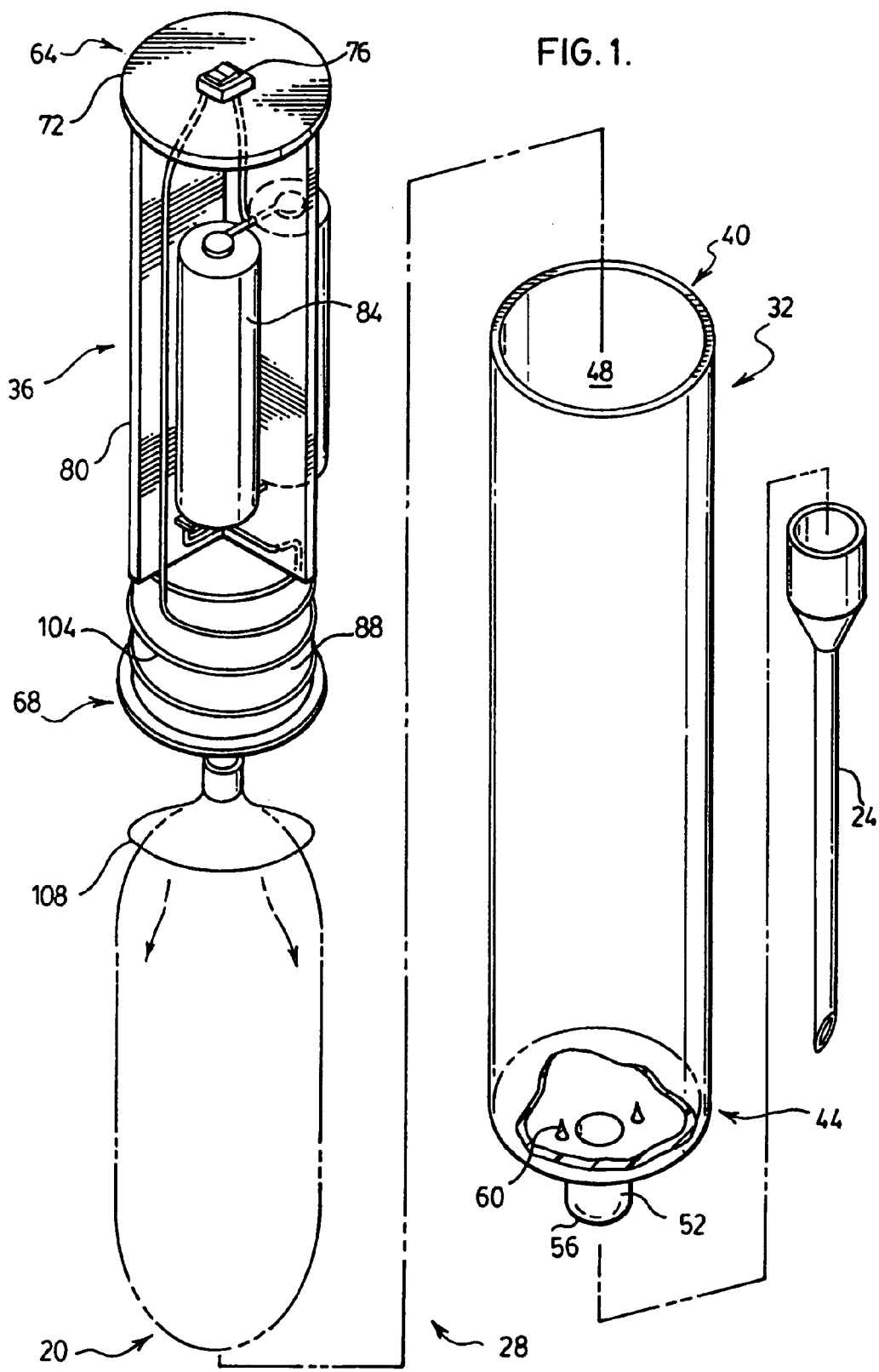
FIG. 1 is a perspective view of an apparatus for administering a therapeutic agent in accordance with an embodiment of the invention.

Referring to FIG. 1, an embodiment of the invention includes an apparatus for administering a therapeutic agent indicated generally at 20. Apparatus 20 includes a needle 24 that attaches to a syringe 28 comprising a hollow barrel 32 for inserting a plunger 36.

A therapeutic agent within barrel 32 can be delivered through needle 24 by depressing plunger 36. Needle 24 is of any desired material, length or gauge that may be desired according to the therapeutic agent being delivered. In a present embodiment, the therapeutic agent is an oxygen-ozone mixture, the details of which will be discussed in greater detail below. In a present embodiment, where syringe 28 is delivering an oxygen-ozone mixture into a herniated disc, then needle 24 can be a Chiba needle or Franceen needle or other suitable needle as will occur to those of skill in the art.

Barrel 32 is made from any suitable material that is substantially rigid and substantially inert when exposed to ozone, such as glass, stainless steel, polycarbonate, high density polyethylene, chlorinated polyvinylchloride, silicone, ethylene-propylene terpolymer, and fluoropolymer materials, such as polytetrafluoroethylene, fluorinated ethylene-propylene, etc. Barrel 32 is substantially cylindrical and characterized by a first end 40 and a second end 44 opposite first end 40. First end 40 is characterized by an opening 48 for receiving plunger 36 therein. Second end 44 is characterized by a cylindrical tip 52 projecting externally from second end 44 and having an outlet 56 with a diameter smaller than opening 48 of first end 40 through which the oxygen-ozone mixture can be delivered. Tip 52 presents a fitting to which needle 24 can attach.

Barrel 32 also includes a pair of piercing members 60 rigidly affixed to second end 44 and projecting internally towards first end 40 of barrel 32. Piercing members 60 are substantially rigid and present a sharp surface for puncturing or piercing a balloon or like expandable, elastic enclosure—as will be explained in greater detail below. It is to be understood, however, that in other embodiments one or more piercing members 60 can be mounted at any location on the interior surface of barrel 32, such as at any suitable location along the interior side wall of barrel 32, and can project internally towards the opposite interior side wall.

Plunger 36 is also made from any suitable material that is substantially inert when exposed to ozone, such as those materials previously mentioned in relation to barrel 32. Plunger 36 is substantially cylindrical for coaxial insertion within barrel 32, and is characterized by a first end 64 and a second end 68 opposite first end 64, wherein second end 68 is configured for insertion into opening 48 of barrel 32. First end 64 is characterized by a thumb-actuator 72 for depression by a surgeon or other medical professional. In a present embodiment, actuator 72 includes an on-off switch 76 mounted at its centre. It is to be understood, however, that in other embodiments switch 76 can be mounted at any location on the surface of actuator 72, such as at the periphery of actuator 72; at any location on the surface of barrel 32; or at any location outside of but connected to syringe 28. Switch 76 can be toggled between "on" and "off" positions.

A shaft 80 projects from actuator 72 towards second end 68. Shaft 80 is characterized by a cross-shaped cross-section, to which a power supply 84 is coaxially mounted. In a present embodiment, power supply 84 is positioned adjacent to actuator 72 between first end 64 and second end 68, and includes two batteries each mounted in parallel with shaft 80 and adjacent to one another between the cross-pieces of shaft 80. Power supply 84 is connected to switch 76 and a generator 88 by electrical wires, such that when switch 76 is in the "on" position current is delivered to generator 88, and when switch 76 is in the "off" position, no current is delivered to generator 88. Power supply 84 is presently preferred to supply an electric current with a voltage between about one volt and about thirty volts, and a more presently preferred voltage between about five volts and about ten volts.

Figure 2:
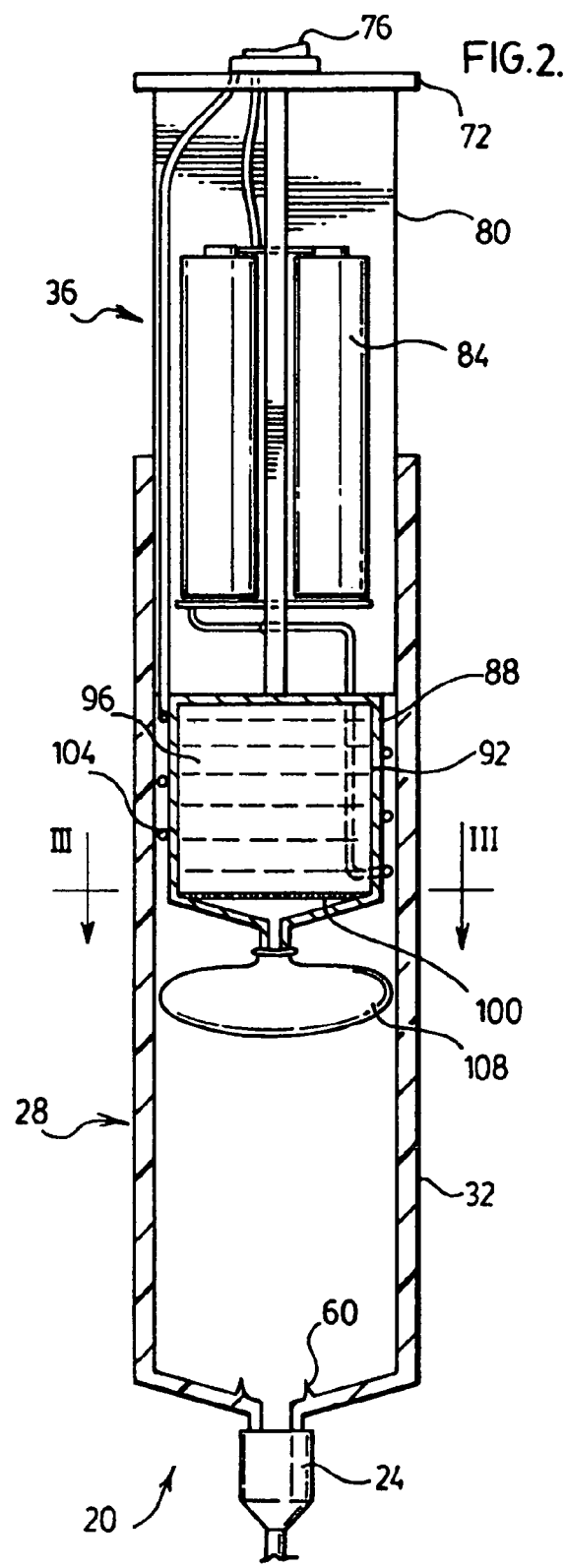
FIG. 2 is a side-sectional view of the apparatus of FIG. 1 in the accumulation configuration.

Generator 88 is mounted to shaft 80 at second end 68. The generator includes electronics to generate and deliver the high-voltage, high-frequency ac electrical signal for producing oxygen-ozone mixtures or excited, energetic, pure oxygen. Referring now to FIGS. 1 and 2, in a present embodiment, generator 88 comprises an open vessel 92 for storing an ozonated gel 96, and a porous membrane 100 covering an open end of vessel 92, the details of which will be explained in greater detail below. Generator 88 also includes a heating element 104 that surrounds the periphery of vessel 92. Element 104 is connected to power supply 84 via switch 76, such that when switch 76 is "on" heating element 104 causes vessel 92 and its contents to increase in temperature.

Gel 96 is made from triacylglycerols or triglycerides which are a mixture of fatty acids such as oleic acid, linoleic acid, and linolenic acid attached to a glycerol backbone; or any combination of fatty acids of the general formula, $CH_3(CH2)_n COOH$ where n is typically an even number between about twelve and about twenty-two attached to a glycerol backbone;, presently preferred to be olive oil [CAS No. 8001-25-0], that can dissolve ozone within gel 96.

The ratio of ozone to olive oil can be delivered in terms of X milligrams of ozone to about one gram of oil, i.e.

$$\frac{X \text{ mg ozone}}{1\text{g olive oil}}$$

X can thus be between about 0.5 and about 1.5; more preferably X can be about 0.7 to about 1.2; more preferably X can be about one.

When gel 96 is heated, a gaseous ozone mixture is created whereby ozone gas is released into the surrounding air. The resulting ozone mixture can be delivered as a ratio in terms of Y micrograms of ozone to about one cubic centimeters of oxygen, i.e.

$$\frac{Y \text{ µg ozone}}{1\text{cm}^3 \text{ oxygen}}$$

Y can be from about five to about one-hundred; more preferably Y can be from about twelve to about forty; more preferably Y can be about twenty.

Gel 96 can be made by sparging the oxygen-ozone mixture, in gaseous form, through the olive oil until the olive oil becomes gelatinous and suitable for refrigeration. Refrigeration temperatures are between about zero ° C. to about five ° C. Gel 96 can be stored at the refrigerated temperature until use. Once in a refrigerated state, gel 96 can be loaded into vessel 92 of generator 88.

An oxygen-ozone mixture can be released from gel 96 upon heating vessel 92, using element 104, to a temperature presently preferred. In the present embodiment, generator 88 is configured to heat the ozonated olive oil to between about twenty ° C. and about eighty ° C.; more preferably between about thirty ° C. and about fifty ° C.; more preferably to about thirty-seven ° C.

Vessel 92 is closed at the end of generator 88 proximal to actuator 72, and is open at the opposite end. The open end of vessel 92 is covered by porous membrane 100, such that generator 88 can communicate with an accumulator 108 attached to second end 68 of plunger 36.

As mentioned above, accumulator 108 is attached to plunger 36 at second end 68, and communicates with generator 88 through membrane 100. In a present embodiment, accumulator 108 is a resiliently deformable balloon, also made from any suitable expandable material that is substantially inert when exposed to ozone, such as those materials previously mentioned in relation to barrel 32. Accumulator 108 has an accumulation configuration wherein accumulator 108 can be expanded from a non-expanded state (as shown in FIG. 1) to an expanded state (as shown in dotted lines in FIG. 1). In addition, accumulator 108 has a delivery configuration wherein accumulator 108 is pierced to allow delivery of its contents out from accumulator 108 and into direct contact with the interior of barrel 32, the details of which will be explained in greater detail below. In FIGS. 1 and 2, switch 76 is shown in the "off" position, and accumulator 108 is shown in an accumulation configuration. With switch 76 in the "off" position, there is substantially no ozone mixture being generated by generator 88, and substantially no ozone mixture being accumulated in accumulator 108. Accumulator 108 is shown in a substantially non-expanded state.

Figure 3:
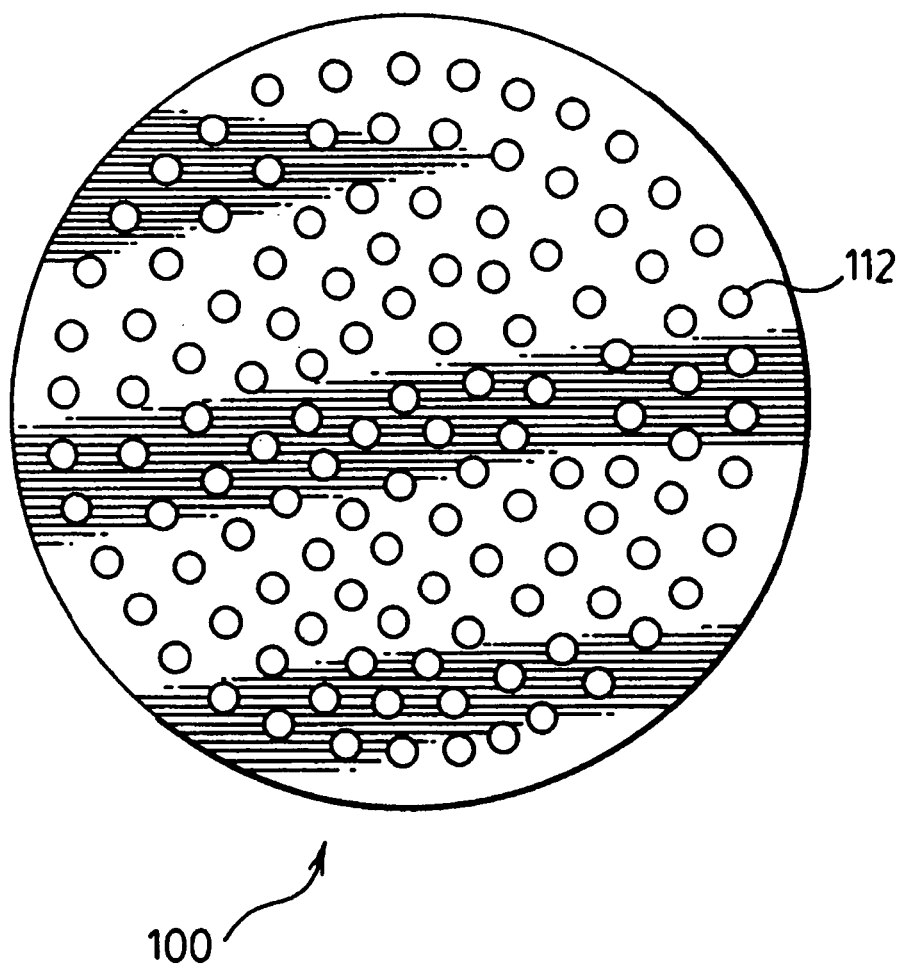
FIG. 3 is a sectional view through lines III-III of FIG. 2 showing the porous membrane in accordance with an embodiment of the invention.

Referring now to FIG. 3, membrane 100 is shown in greater detail, which is derived from a sectional view through the dotted line labelled as III-III in FIG. 2 of syringe 28. Membrane 100 is disposed between generator 88 and accumulator 108, and includes substantially circular pores 112 which allow the ozone mixture that is generated by generator 88 to move from generator 88 through membrane 100 and into accumulator 108, while retaining the remaining gel 96 within generator 88. The diameter of pores 112 in FIG. 2 is merely for illustration purposes and is not to scale, but rather intended to denote that the ozone mixture can pass through such pores while leaving gel 96 within vessel 92. In a present embodiment, membrane 100 is made from porous ceramic or glass that is gas permeable, but not liquid permeable. It should be understood, however, that in certain embodiments, membrane 100 can be omitted altogether.

Figure 4:
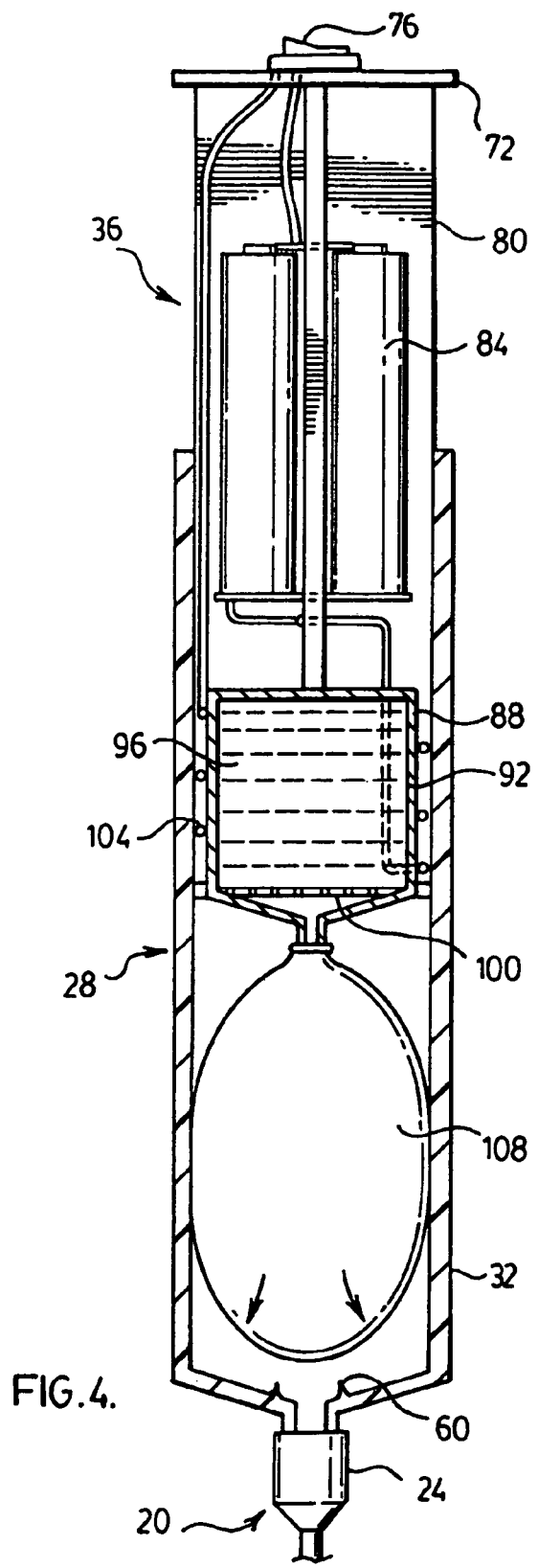
FIG. 4 is a side-sectional view of the apparatus of FIG. 2 in the accumulation configuration showing expansion of the accumulator.

In operation, apparatus 20 is removed from refrigeration just prior to use. Plunger 36 is received within opening 48 of barrel 32, and needle 24 is attached to tip 52 of barrel 32. Referring now to FIG. 4, switch 76 is moved to the "on" position and an electric current is produced by power supply 84. Power supply 84 provides the electric current through electrical wires to activate heating element 104. Upon activation, heating element 104 heats vessel 92 of generator 88, which in turn heats gel 96 to a temperature as noted above, but presently more preferred to be about 37° C. Such heating results in generation of an ozone mixture that is released from gel 96. As the ozone mixture is released from gel 96, the ozone mixture travels towards the open end of vessel 92 and membrane 100. The ozone mixture travels through pores 112 of membrane 100 and into accumulator 108, while gel 96 remains in vessel 92. Accumulator 108 becomes filled with the ozone mixture and expands from a non-expanded state to an expanded state.

Figure 5:
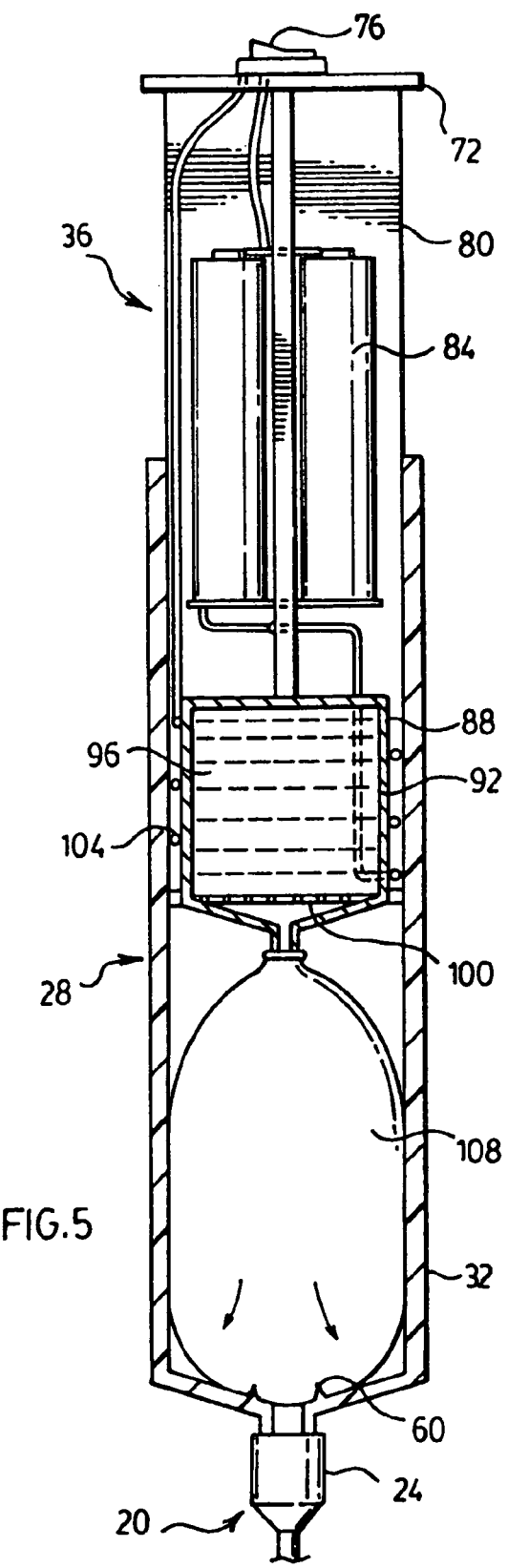
FIG. 5 is a side-sectional view of the apparatus of FIG. 4 in the accumulation configuration showing further expansion of the accumulator.

Referring to FIG. 5, as switch 76 remains in the "on" position and the ozone mixture continues to accumulate within accumulator 108, accumulator 108 continues to expand towards second end 44 of barrel 32 and comes into contact with piercing members 60.

Figure 6:
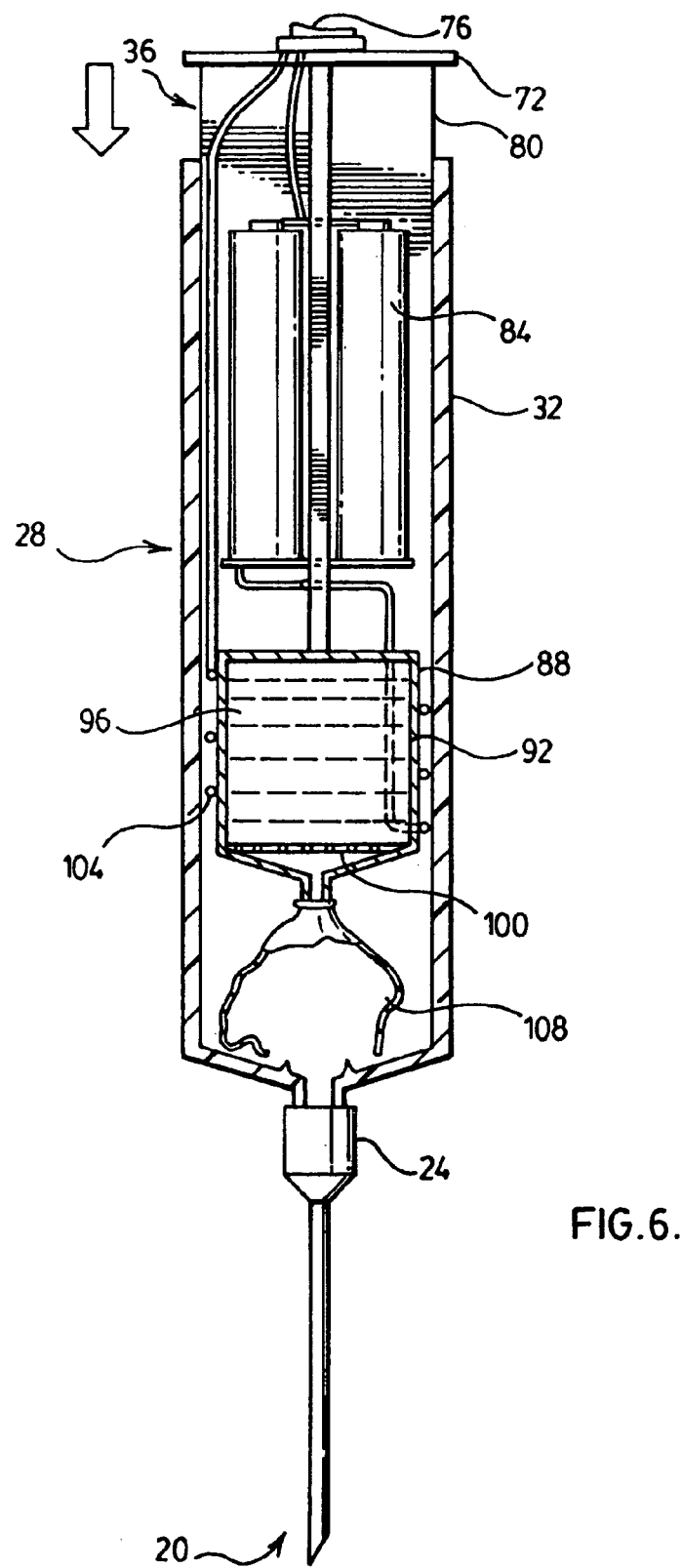
FIG. 6 is a side-sectional view of the apparatus of FIG. 5 in the delivery configuration.

Referring to FIG. 6, as switch 76 remains in the "on" position and accumulator 108 continues to expand towards second end 44 of barrel 32 and into piercing members 60, accumulator 108 is pierced by piercing members 60 and moves into a delivery configuration. The oxygen-ozone mixture is released out from accumulator 108 and into the interior of barrel 32.

Figure 7:
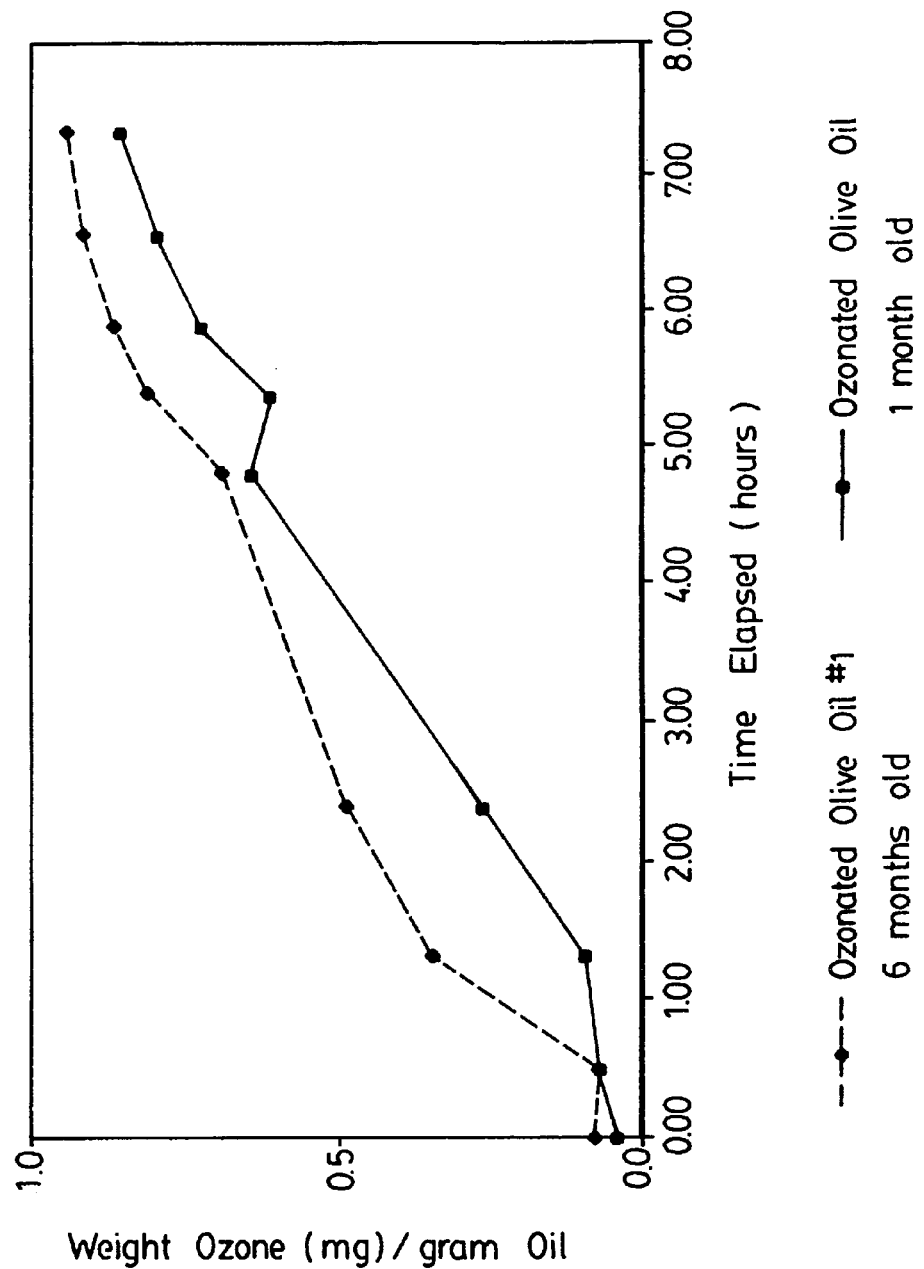
FIG. 7 shows a graph for release of ozone gas when one gram of ozonated olive oil is heated to 37° C.

Once barrel 32 is filled with the oxygen-ozone mixture, switch 76 can be moved to the "off" position, and apparatus 20 positioned for use for the delivery of the ozone mixture to a patient. Needle 24 can be inserted into a patient's tissue (such as into a disk herniation, or other target area) where the oxygen-ozone mixture is to be administered. Having inserted needle 24 into the target area, actuator 72 is depressed towards second end 44 of barrel 32, and the oxygen-ozone mixture is delivered from barrel 32, through outlet 56 and needle 24, and into the target area. The graph of FIG. 7 illustrates an example where a gel suitable for use as gel 96 was heated to release an oxygen-ozone mixture over time. In this example, a plurality of one gram samples of ozonated olive oil gels, each of varying ages, are added to one-hundred ml of indigo reagent (i.e. 0.6 g/L potassium indigo trisulfonate in 20 mM phosphoric acid) solution and heated to a temperature of about 21.5° C. The weight of ozone in mg/gram olive oil is delivered as a function of time. After about seven and a half hours at a temperature of about 21.5° C., about 0.95 mg/gram olive oil of ozone was released from the older gel (about six months old), and about 0.85 mg/gram olive oil of ozone was released from the younger gel (about twenty-four days old).

As will become apparent from the teachings herein, generator 88 is simply one example of a generator that can be used in accordance with the present invention. Indeed the teachings herein can be applicable to any generator for producing an oxygen-ozone mixture.

A variation of generator 88 includes an electrochemical cell ozone generator, comprising an anode, a cathode, a cationic membrane and an electrolyte. An oxygen-ozone mixture can be released from the electrochemical cell through the electrolysis of water and the production of ozone and oxygen at the anode, at an electric current with a presently preferred voltage between about three volts and about twenty volts and a more presently preferred voltage between about two volts and about ten volts; and at a presently preferred temperature between about five ° C. and about fifty ° C., and a more presently preferred temperature between about fifteen ° C. and about thirty ° C.

A modified version of apparatus 20 is illustrated in FIGS. 8-11, which is indicated generally at 20*a*. Apparatus 20*a* includes many of the same elements as apparatus 20, and like elements in apparatus 20*a* bear the same reference as their counterparts in apparatus 20, except that they are followed with the suffix "a".

Of notable exception, however, is that apparatus 20*a* does not include a balloon accumulator in communication with generator 88*a*; and also does not include piercing members in barrel 32*a*. In addition, and as will be explained in more detail below, the interior 116*a* of barrel 32*a* is of a different configuration than the interior of barrel 32, in that interior 116*a* comprises a second end 120*a* that is disposed at a position within barrel 32*a* that is different from that of second end 44*a* of barrel 32*a*. In further contrast to apparatus 20, apparatus 20*a* also includes a moveable stopper 124*a*, that is movable within interior 116*a*. Apparatus 20*a* also includes an outport channel 128*a* and an air vent 132*a* disposed within barrel 32*a*. Furthermore, generator 88*a* of the present embodiment is of a different configuration than generator 88 of apparatus 20, (although in other embodiments need not be different) in that generator 88*a* does not include a heating element, gel, membrane or vessel. Generator 88*a* is selected from one of a corona discharge device, an electrochemical cell ozone generator, and an ultraviolet light source or combination thereof.

Figure 8:
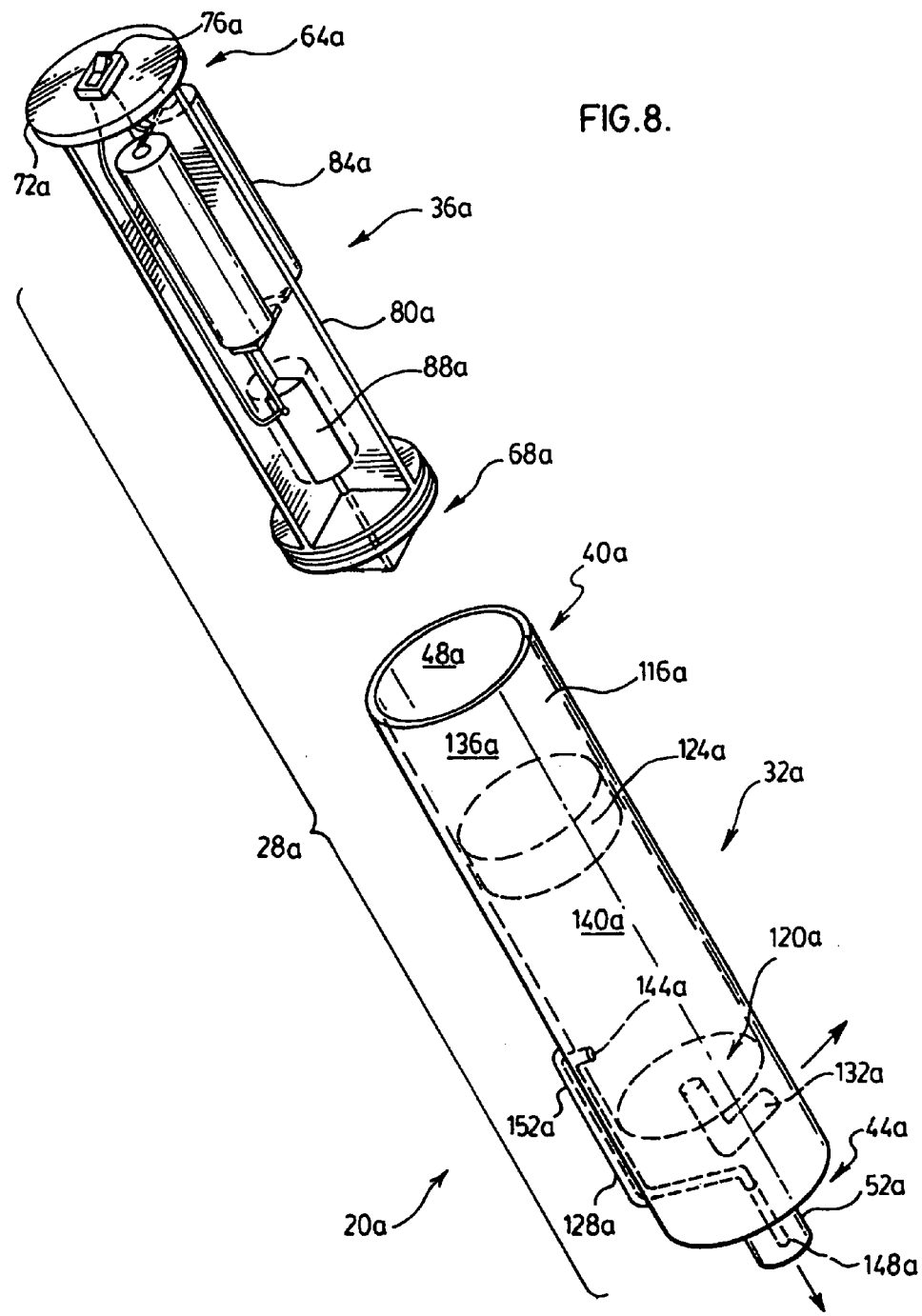
FIG. 8 is a perspective view of an apparatus for administering a therapeutic agent in accordance with another embodiment of the invention.

Referring now to FIG. 8, interior 116*a* is coaxially disposed within barrel 32*a* from first end 40*a* towards second end 44*a* of barrel 32*a*. Interior 116*a* is substantially cylindrical and is characterized by second end 120*a* being disposed at a position between first end 40*a* and second end 44*a* of barrel 32*a*. Second end 120*a* is proximal to second end 44*a* of barrel 32*a*.

A moveable stopper 124*a* is disposed within interior 116*a*. Stopper 124*a* is resiliently deformable, is made from any suitable material such was suggested for plunger 36, is substantially disc-shaped, having an exterior diameter slightly larger than the interior diameter of interior 116*a*, much in the same manner a traditional plunger tip is complementary to the interior of a traditional syringe barrel. Stopper 124*a* forms a substantially air-tight seal with the adjacent inner wall of interior 116*a*, and is moveable from a position proximal to first end 40*a* of barrel 32*a* towards a position proximal to second end 120*a* of interior 116*a*. In addition, stopper 124*a* divides interior 116*a* into a first chamber 136*a* and a second chamber 140*a*.

First chamber 136*a* is defined by the space between stopper 124*a* and second end 68*a* of plunger 36*a* received within interior 116*a*. Second chamber 140*a* is defined by the space between stopper 124*a* and second end 120*a* of interior 116*a*. First chamber 136*a* can communicate with generator 88*a* through a nozzle at second end 68*a* of plunger 36*a*. According to the movement of plunger 124*a*, first chamber 136*a* has an accumulation configuration wherein first chamber 136*a* can be expanded along the length of interior 116*a*, and second chamber 140*a* can be contracted correspondingly. When first chamber 136*a* is in the accumulation configuration, only second chamber 140*a* can communicate with outport channel 128*a* attached to the side wall of interior 116*a* proximal to second end 120*a* of interior 116*a*. In addition, first chamber 136*a* has a delivery configuration wherein stopper 124*a* is positioned at or proximal to second end 120*a* of interior 116*a* to allow communication between first chamber 136*a* and outport channel 128*a*.

Outport channel 128*a* includes an inlet 144*a* and an outlet 148*a* connected by a passageway 152*a* disposed within barrel 32*a*. Inlet 144*a* of channel 128*a* is disposed at the sidewall of interior 116*a* at a position between first end 40*a* of barrel 32*a* and second end 120*a* of interior 116*a*, and proximal to second end 120*a* of interior 116*a*. Outlet 148*a* of channel 128*a* is disposed within tip 52*a*. Passageway 152*a* is substantially hollow and tubular in configuration, and extends from inlet 144*a* along the sidewall of barrel 32*a* towards second end 44*a* and across the base of barrel 32*a* at second end 44*a* towards tip 52*a* to outlet 148*a*. An air vent 132*a* includes an inlet (shown, but not marked in the figures) and an outlet (shown, but not marked in the figures) connected by a passageway disposed within barrel 32*a*. The inlet of air vent 132*a* is disposed at the base of interior 116*a* at second end 120*a*. The outlet of air vent 132*a* is disposed at the sidewall of barrel 32*a* at a position between second end 120*a* of interior 116*a* and second end 44*a* of barrel 32*a*. The passageway of air vent 132*a* is substantially hollow and tubular in configuration, and extends from the inlet of air vent 132*a* through the base of barrel 32*a* towards second end 44*a* and across the base of barrel 32*a* at second end 44*a* to the outlet of air vent 132*a*.

Figure 9:
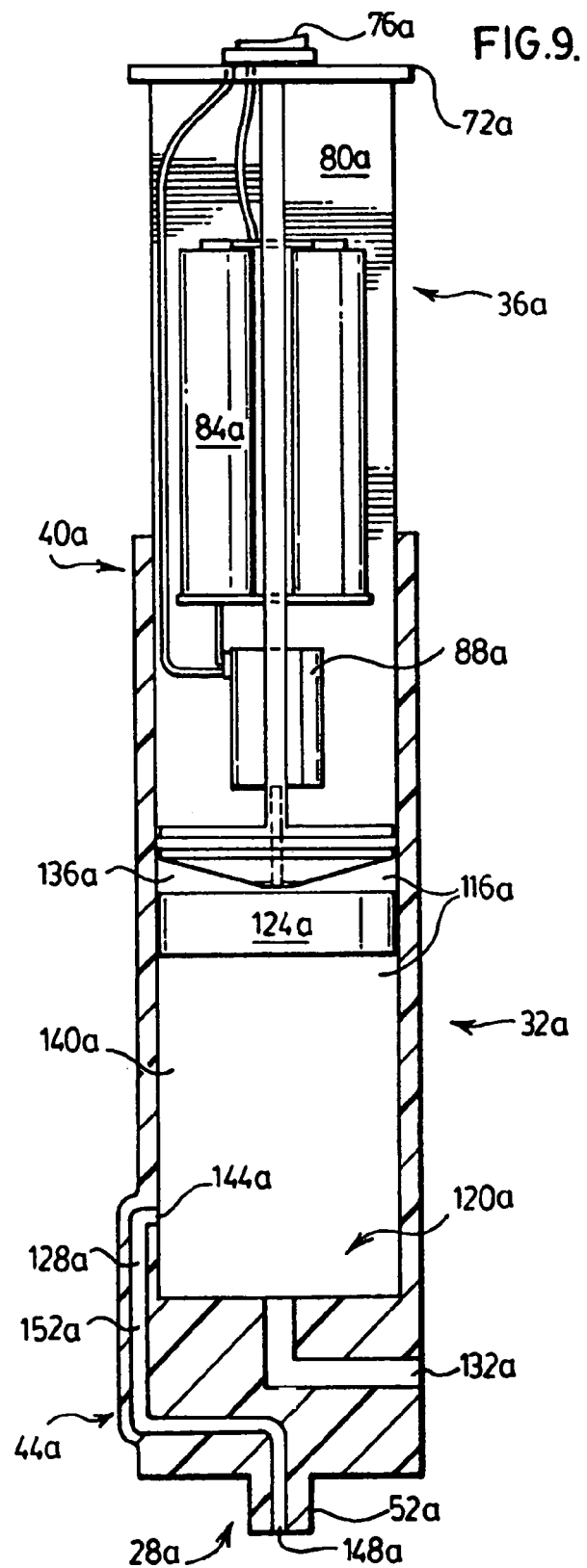
FIG. 9 is a side-sectional view of the apparatus of FIG. 8 in the accumulation configuration.
Figure 10:
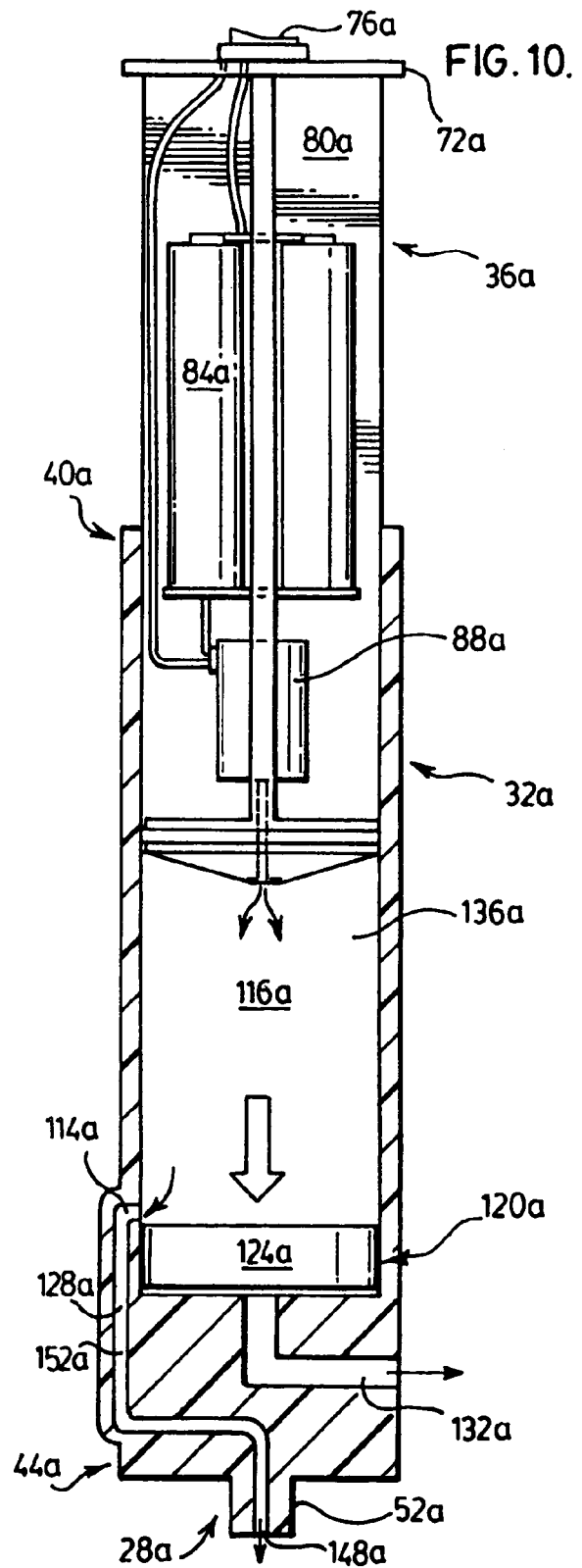
FIG. 10 is a side-sectional view of the apparatus of FIG. 9 in the delivery configuration.

In operation, plunger 36*a* is received within opening 48*a* of barrel 32*a*, and needle 24*a* is attached to tip 52*a* of barrel 32*a*. Referring to FIG. 9, operation begins with first chamber 136*a* in an accumulation configuration and stopper 124*a* positioned between first end 40*a* of barrel 32*a* and outport channel 128*a* such that only second chamber 140*a* can communicate with outport channel 128*a*. Switch 76*a* is moved to the "on" position and an electric current is produced by power supply 84*a*. Power supply 84*a* provides the electric current through electrical wires to activate generator 88*a*. Upon activation, generator 88*a* generates an oxygen-ozone mixture that is released through the nozzle of plunger 36*a* at second end 68*a* and into first chamber 136*a* of interior 116*a* of barrel 32*a*. Referring to FIG. 10, when first chamber 136*a* is filled with the accumulating oxygen-ozone mixture generated from generator 88*a*, stopper 124*a* is urged towards second end 120*a* by the force of the accumulating oxygen-ozone mixture in first chamber 136*a*. As stopper 124*a* is urged towards second end 120*a* of interior 116*a* by the accumulating oxygen-ozone mixture, and first chamber 136*a* is expanded, second chamber 140*a* contracts correspondingly along the length of interior 116*a*. As second chamber 140*a* is contracted, the air within second chamber 140*a* is urged out through air vent 132*a*. As switch 76*a* remains in the "on" position and stopper 124*a* continues to be urged to second end 120*a* of interior 116*a*, first chamber 136*a* moves from an accumulation configuration into a delivery configuration (as shown in FIG. 10), whereby first chamber 136*a* can communicate with outport channel 128*a*.

Figure 11:
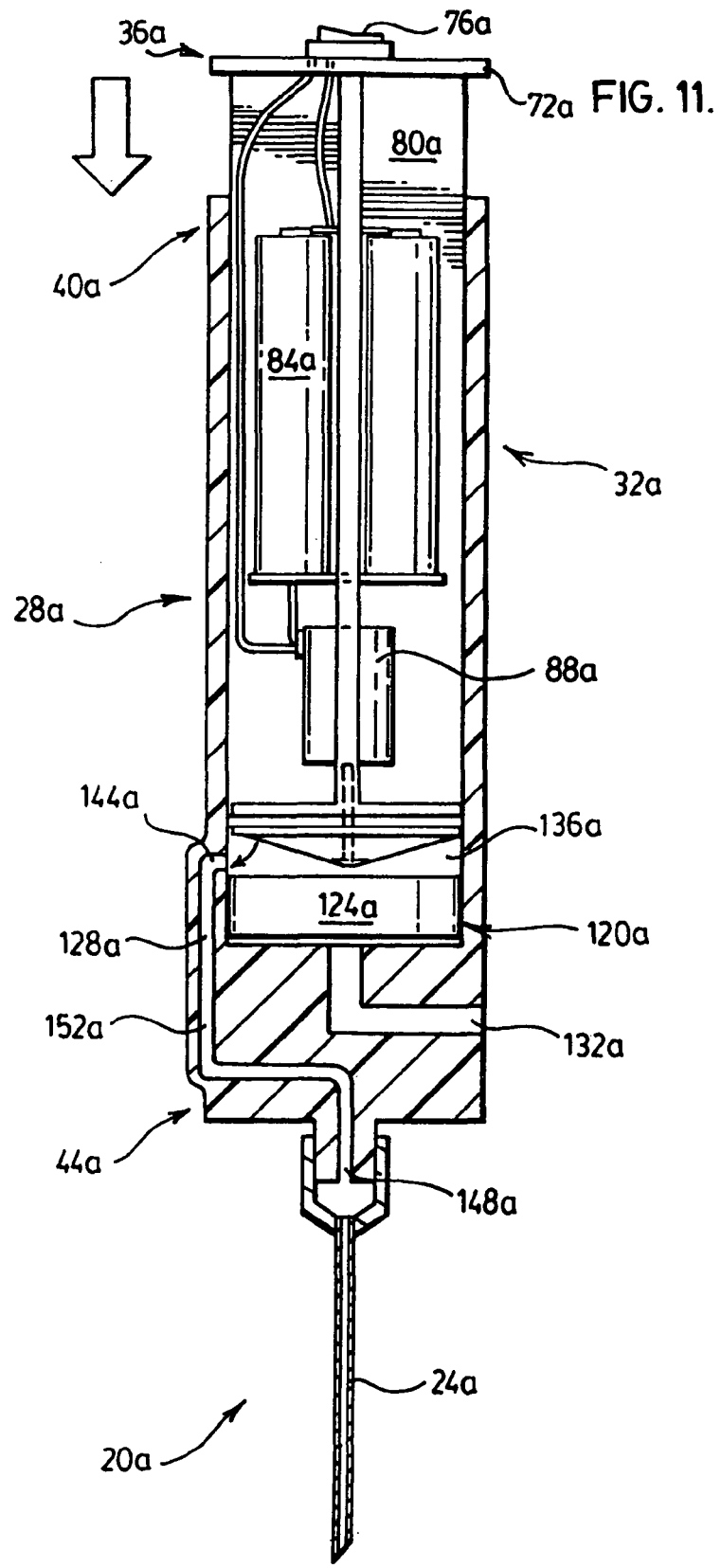
FIG. 11 is a side-sectional view of the apparatus of FIG. 10 in the delivery configuration showing depression of the plunger.

Referring now to FIG. 11, once first chamber 136*a* is in the delivery configuration and is filled with the oxygen-ozone mixture, switch 76*a* can be moved to the "off" position, and apparatus 20*a* positioned for use for the delivery of the oxygen-ozone mixture to a patient. Needle 24*a* can be inserted into a patient's tissue (such as into a disk herniation, or other target area) where the oxygen-ozone mixture is to be administered. Having inserted needle 24a into the target area, actuator 72a of plunger 36a is depressed towards second end 120a of interior 116a of barrel 32a, and the oxygen-ozone mixture is delivered out from first chamber 136a, through outport channel 128a and needle 24a, and into the target area.

Figure 12:
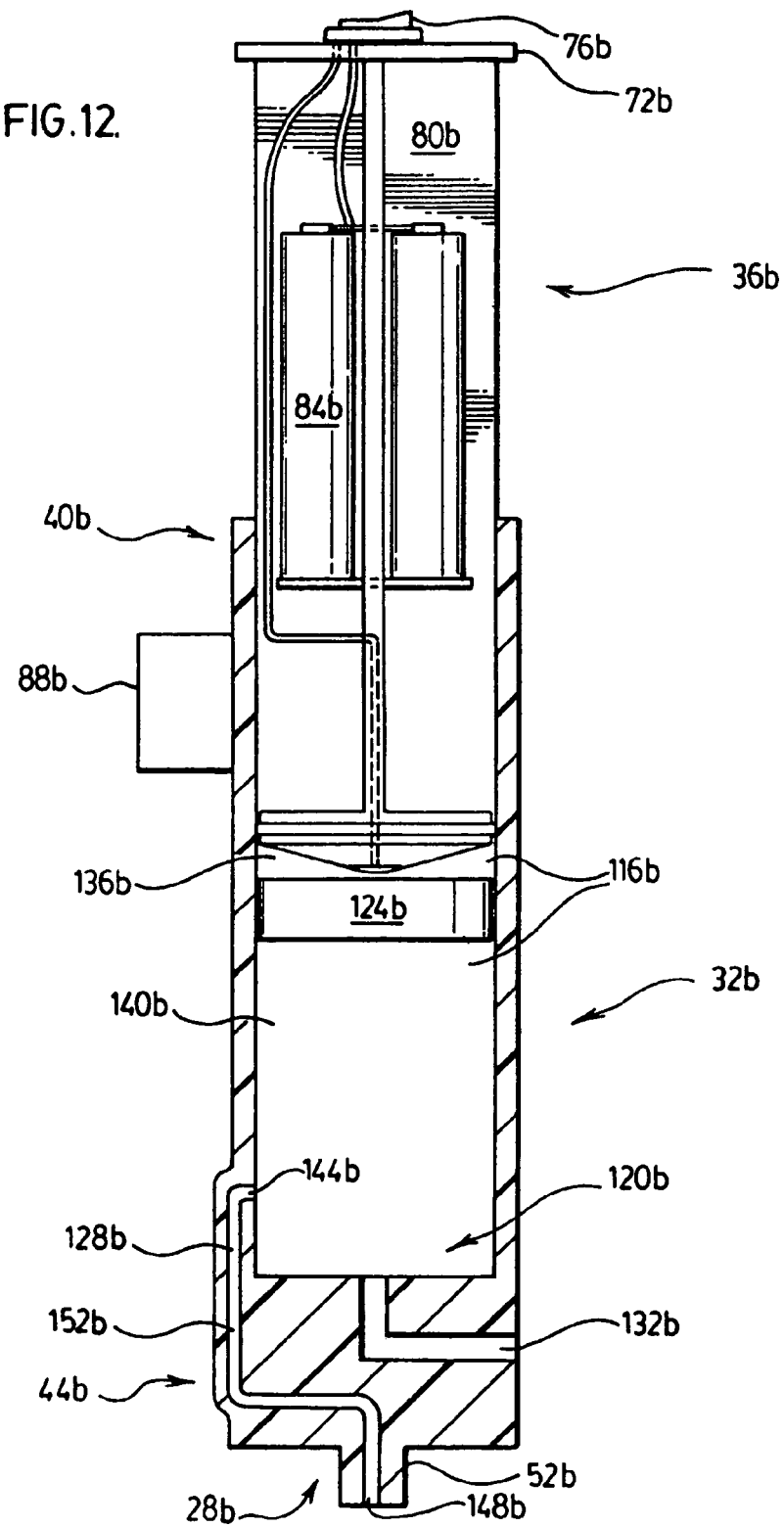
FIG. 12 is a side-sectional view of an apparatus for administering a therapeutic agent in accordance with another embodiment of the invention; and, FIG. 13 is a side-sectional view of an apparatus for administering a therapeutic agent in accordance with another embodiment of the invention.

A modified version of apparatus 20a is illustrated at FIG. 12, which is indicated generally at 20b. Apparatus 20b includes the same elements as apparatus 20a, bearing the same reference as their counterparts in apparatus 20a, except that they are followed with the suffix "b". Of notable exception, however, is that generator 88b of apparatus 20b is attached to the exterior surface of barrel 32b of syringe 28b, in contrast to generator 88a of apparatus 20a which is attached to plunger 36a.

Figure 13:
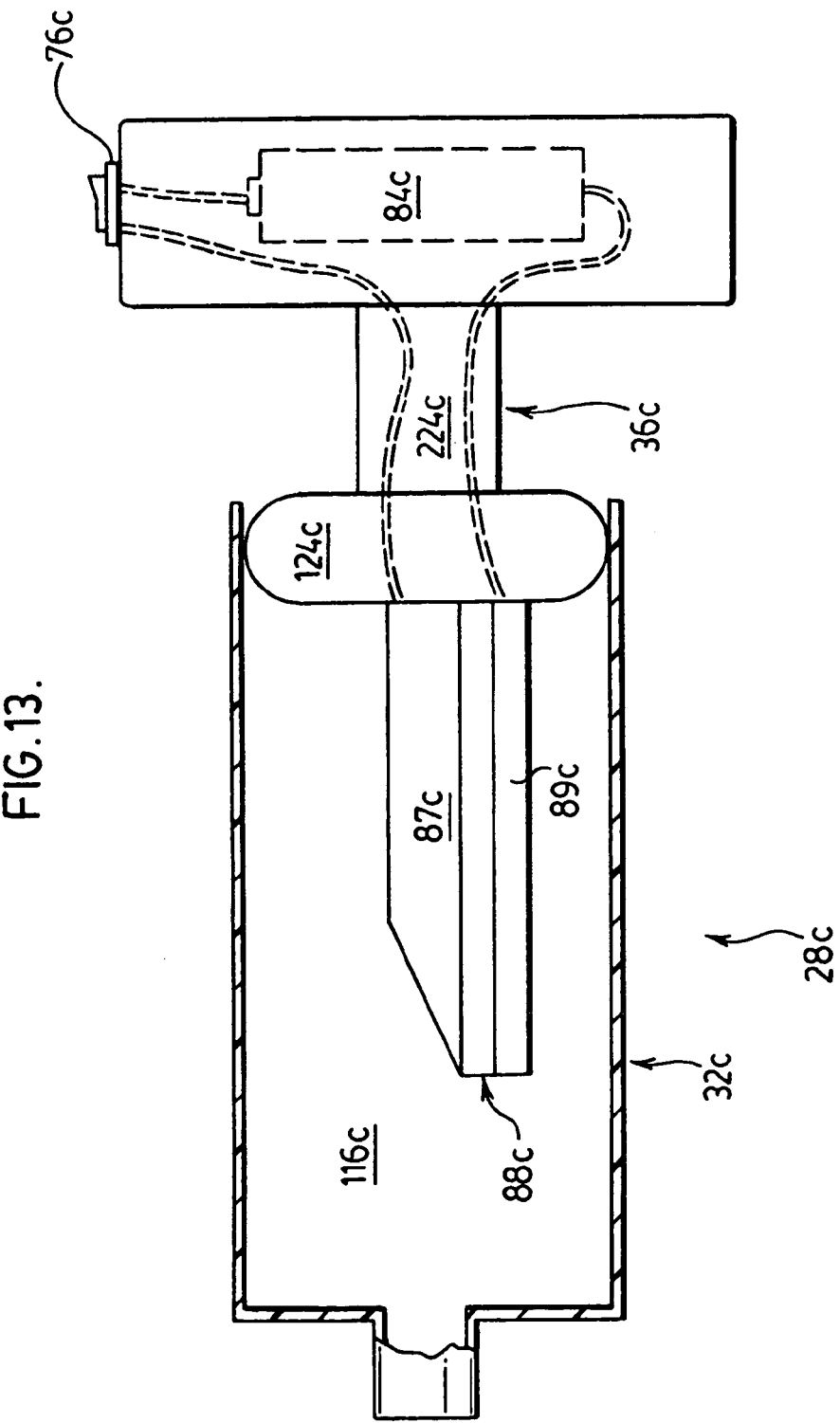

Another modified version of apparatus 20a is illustrated at FIG. 13, which is indicated generally at 20c. A variation of generator 88 includes a corona discharge device 88c comprising a dielectric 87c, and an electrode 89c. Device 88c can be used to produce an oxidizing gas. For example, device 88c can be for exposure to an oxygen-containing gas within interior 116c of barrel 32c. The gas can be pure oxygen gas. For example, an oxygen-ozone mixture can be released from the corona discharge device 88c by passing the oxygen-containing gas through an electrical field originating from device 88c at a presently preferred frequency between about one-tenth kilohertz ("kHz") and about one thousand kHz, at a more presently preferred frequency between about twenty kHz and about sixty kHz; at an electric current with a presently preferred voltage between about one kilovolt and about twenty kilovolts and a more presently preferred voltage between about three kilovolts and about six kilovolts; and at a presently preferred temperature between about fifteen ° C. and about thirty ° C., and a more presently preferred temperature between about twenty ° C. and about twenty-five ° C. The electrical power according to the aforementioned parameters of frequency and voltage (or otherwise desirable parameters) is delivered by a power supply 84c that is so configured to generate an electrical signal for device 88c according to those parameters. Power supply 84c can be activated and deactivated using switch 76c.

In use, apparatus 20c is in the position shown in FIG. 13. Next, switch 76c is activated thereby causing device 88c to emit a field that interacts with the oxygen in interior 116a, and thereby create ozone. Once the ozone generation cycle is complete, plunger 36c is depressed to deliver ozone from the end of barrel 32c. Of note, in the present embodiment the stroke of plunger 36c is chosen so that, when fully depressed, device 88c may come into close proximity of the distal end of barrel 32c, but without actually coming into contact therewith.

It should be understood that the configuration of device 88c is merely exemplary and other configurations of a corona discharge device are contemplated.

While only specific combinations of the various features and components of the present invention have been discussed herein, it will be apparent to those of skill in the art that desired subsets of the disclosed features and components and/or alternative combinations of these features and components can be utilized, as desired. For example, other types of pain can be treated using the teachings herein. For example, joints, tendons, ligaments are other areas that can be treated. Another example includes irrigating a wound site, such as a colostomy, with the therapeutic agent to reduce pain at the wound site. An another example is to irrigate a subcutaneous pouch for holding a pacemaker or the like for sterilization and/or treatment of pain and/or decrease of inflammation and such other advantage corresponding to the therapeutic agent as will occur to those of skill in the art. Furthermore, it is to be understood that the therapeutic agent can include any suitable oxygen-ozone mixture or any other suitable therapeutic agent known to those of skill in the art. Furthermore, it should be understood that the apparatus of the present invention can be in any desired size or shape or configuration. In addition, certain embodiments of the apparatus also include a plunger and a hollow barrel for slidably receiving the plunger. It should be understood that the plunger and the barrel of the apparatus can be of any desired complementary size or shape. It should also be apparent that components of embodiments herein can be combined. For example, either plunger 36 or plunger 36a can be used with any one of barrel 32 and barrel 32a.

Furthermore, it is to be understood that the generator of the present invention can be in any desired size, shape or form. For example, in the embodiments discussed above, the generator included one of a generator comprising an ozonated gel, (e.g. generator 88), a corona discharge device, an electrochemical cell, an ultraviolet light source. However, in other embodiments, the generator can be any suitable generator for producing a desired gaseous therapeutic agent.

The gaseous therapeutic agent can be an oxidizing gas or an inert gas or combinations thereof.

An oxidizing gas which can include oxygen ($O_2$); a mixture containing oxygen plus ozone ($O_3$); oxygen radicals; hydroxyl radicals; ionic oxygen; oxygen treated with energy; and/or combinations any of the foregoing.

Inert gases can include, but are not limited to, nitrogen, helium, carbon dioxide, and/or combinations thereof.

Furthermore, it is to be understood that the generator can be disposed at any suitable position relative to the syringe of the apparatus. For example, the generator can be disposed at any suitable location within the syringe of the apparatus, such as at any location between the first end and the second end of the plunger, or at any location between the first end and the second end of the interior of the barrel. In addition, the generator can also be disposed at any suitable location on the exterior surface of the syringe (as shown in FIG. 12), or at a location outside the syringe where the generator is unattached to but connected to the syringe.

Furthermore, it is to be understood that the accumulator of certain embodiments, and the first chamber of certain other embodiments of the present invention as discussed above, can be of any desired size, shape or form. For example, in the embodiments discussed above, the accumulator included a resiliently deformable balloon. However, in other embodiments, the accumulator can be any bag, container, vessel, chamber or the like that is movable from an accumulation configuration to a delivery configuration. In addition, the first chamber of the present invention can be in any configuration wherein the first chamber is movable from an accumulation configuration to a delivery configuration. Furthermore, it is to be understood that the power supply of the present invention can be in any desired size, shape or form. For example, in the embodiments discussed above, the power supply included two batteries each mounted in parallel with the shaft of the plunger, adjacent to one another between the cross-pieces of the shaft, and positioned adjacent to the actuator between the first end and the second end of the plunger. However, in other embodiments, the power supply can include one or more batteries mounted in any suitable configuration and at any suitable location between the first end and the second end of the plunger; between the first end and the second end of the barrel, on the exterior surface of the syringe. Alternatively, the power supply can actually be external to the syringe, and connectable to the syringe at the time of ozone generation. By the same token, both the heating element and power supply can be omitted in lieu of providing a syringe capable of having heat applied to the ozone generator through an external heat source in order to generate the oxygen-ozone mixture.

Furthermore, it is to be understood that the outport channel of certain embodiments of the present invention can be of any desired size, shape or form. For example, the inlet of the outport channel can be disposed at any suitable location between the first end and the second end of the interior of the barrel. In addition, the passageway of the outport channel can include portions that extend along the outside of the sidewall of the barrel, and/or portions that extend within the sidewall of the barrel.

Furthermore, it is to be understood that the air vent of certain embodiments of the present invention can be of any desired size, shape or form. For example, the inlet of the air vent can be disposed at any suitable location on the base of the interior of the barrel at the second end of the barrel, or at any suitable location on the interior side wall of the barrel between the stopper and the second end of the barrel. In addition, the outlet of the air vent can be disposed at any suitable location on the sidewall of the barrel between the first end and the second end of the barrel; at the base of the barrel at the second end of the barrel; or at the tip of the barrel.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A syringe comprising:
 a barrel;
 a plunger having a nozzle end for insertion into a first end of said barrel and an actuator end to extend out of the barrel, wherein the plunger is configured to facilitate delivering an oxidizing gas from a second end of said barrel;
 a corona-discharge device within said barrel for producing said oxidizing gas, wherein said corona-discharge device comprises a housing mounted to the plunger, between the nozzle end and the actuator end of the plunger, wherein the housing is configured to expel said oxidizing gas exclusively through the nozzle end of the plunger into a space formed within the barrel, between the nozzle end of the plunger and the second end of the barrel, and to prevent the oxidizing gas from occupying a space within the plunger between the housing and the actuator end of the plunger;
 an accumulator chamber defined within said barrel holding oxygen and having an accumulation configuration in communication with said generator for producing said oxidizing gas from said oxygen when said accumulator chamber is in said accumulation configuration; and
 said accumulator chamber having a delivery configuration for expressing said oxidizing gas from said second end when a desired level of oxidizing gas has been generated in said accumulator chamber.

2. The syringe of claim 1, further comprising a power supply located external to the syringe.

3. The syringe of claim 1, further comprising a power supply located within the plunger between the first and second end of the plunger.

4. The syringe of claim 1, further comprising a power supply located within the barrel between the first and second end of the barrel.

5. The syringe of claim 1, further comprising a power supply located on the exterior surface of the syringe.

6. The syringe of claim 1, further comprising a power supply that is connectible to the syringe at the time of ozone generation.

* * * * *